US00PP10855P

United States Patent [19]

LaCourse et al.

[11] Patent Number: Plant 10,855

[45] Date of Patent: Apr. 13, 1999

[54] CENIZO SHRUB NAMED 'BERTSTAR DWARF'

[76] Inventors: Jeffrey M. LaCourse, 5713 Dry Creek Pass, San Antonio, Tex. 78250; Bert L. Thomas, Jr., 3300 Sage Rd. #3204, Houston, Tex. 77056

[21] Appl. No.: 08/799,069

[22] Filed: Feb. 11, 1997

[51] Int. Cl.[6] ..... A01H 5/00

[52] U.S. Cl. ..... Plt./54.1

[58] Field of Search ..... Plt./54.1

[56] References Cited

PUBLICATIONS

Henrickson, J. and L.D. Flyr. 1985. Systematics of Leucophyllum and Eremogeton (Scrophulariaceae), Sida 11:107–172.

Nesom, G.L. 1991. A new species of Leucophyllum (Scrophulariaceae) from Nuevo Leon, Mexico, Phytologia 71:337–339.

Nesom, G.L. 1993. Leucophyllum alejandrae (Scrophulariaceae), a new gypsophilic species from Nuevo Leon, Mexico. Phytologia 74:293–295.

*Primary Examiner*—Elizabeth C. Kemmerer

*Attorney, Agent, or Firm*—Miller, Sisson, Chapman & Nash, P.C.

[57] ABSTRACT

A variety of Cenizo shrub (*Leucophyllum frutescens*) having small, distinctively globose habit and dense and persistent leafiness. The variety is propagated by tip cuttings and is versatile as an evergreen shrub for use in landscapes.

4 Drawing Sheets

BACKGROUND OF THE INVENTION

The present invention relates to a new and distinct variety of Cenizo shrub (*Leucophyllum frutescens*) which was discovered in a population of containerized *Leucophyllum frutescens* "Compacta" at Turkey Creek Farms, Travis County, Austin, Tex. The invention is derived from a two year old plant initially selected in March 1991 for further evaluation and transplanted to a landscape on the Turkey Creek site. It has been successfully asexually propagated at facilities of Lone Star Growers in San Antonio, Tex., using a quick dip of 1% solution of IBA on semi-hardwood tip cuttings, placed under mist, April through September. The rooting percentage is 90% to 95%.

The genus Leucophyllum comprises 14 species distributed mostly in Mexico. *Leucophyllum frutescens* is the most geographically wide-ranging species of the genus as well as the one with the most northerly distribution. It is the only one reaching into south-central Texas in its native distribution. No formal taxonomic varieties have been recognized within *Leucophyllum frutescens*.

Plants of the typical (wild) form of *Leucophyllum frutescens* have commonly been planted as ornamentals throughout the southwestern United States in relatively frost-free regions. Several distinctive varieties derived from it also are widely marketed and grown. The following varieties have been selected and named by the Texas Agricultural Experiment Station over the last fifteen years:

(a) "White Cloud" is a gray-leaved form with white flowers;
(b) "Green Cloud" is primarily distinguished from wild Cenizo by the reduced amount of leaf pubescence, which gives it a greener color;
(c) "Compacta" is distinguished from wild forms by its reduced size; and
(d) "Rain Cloud" is a gray leaved form with light pink flowers.

BRIEF SUMMARY OF THE INVENTION

The new variety of Cenizo shrub is clearly identified as the species *Leucophyllum frutescens* in the nature and distribution of vestiture, leaf shape and size, and flower size. The new variety, however, is sharply different from the wild forms and equally as distinctive as the above mentioned varieties. The name proposed for the new variety "Bertstar Dwarf" has been coined from the names of one of the inventors, Bert Thomas, who selected the plant, and Lone Star Growers, of San Antonio, Tex., who were the propagators. The inventor at Lone Star Growers is Jeff LaCourse.

The plant is characterized by its small, globose habit and dense and persistent leafiness. The dwarf nature and dense habit make the plant versatile for low foundational plantings and formal landscapes. The persistent foliage at the lower portions of the plant extends through the winter months in Texas. The plant is a vigorous grower and does not exhibit the extreme sensitivity to high humidity or over watering noted with existing varieties of *Leucophyllum frutescens*.

Compared to previously known forms of *Leucophyllum frutescens*, the present invention is shorter with a globose, distinctly more compact habit. The leaves and branches are more densely arranged and the lateral and lower branches are persistently leafy.

The globose, densely leafy aspect of the plant is correlated with the following set of growth characteristics, which differ from those of other forms of Cenizo (compared in Table I with "Compacta"):

(a) shorter height (Table I);
(b) greater number of lateral buds, resulting in leaves and branches in greater density (a greater number of lateral buds per unit length of stem—shorter internodes) (Table I);
(c) partial inhibition of terminal growth of main stems, with correspondingly increased elongation of stems from lateral buds, especially near the branch tips (Table I); and
(d) persistence of leaves and lateral branches on the lower and proximal portions of branches (see sheet 4 photograph).

TABLE I

| Average plant height (cm) | "Berstar" 46 to 48 inches | "Compacta" 72 to 94 inches |
|---|---|---|
| Number of lateral buds per 5 cm on branches 4–8 mm wide | 6–10 | 4–7 |
| Lateral branch length (cm) on distal 5 cm of main branches | 1–3 | no elongation |
| Lateral branch length (cm) on distal 15 cm of main branches | 10–15 | 2–4 |

In other forms of cultivated Cenizo, the main stems are more conspicuously elongated and the lower and lateral branches become relatively bare of leaves, which persist mostly near the branch tips. The "Compacta" variety has neither the globose shape nor distinctive persistence of leaves characteristic of the present plant.

BRIEF DESCRIPTION OF THE DRAWINGS

Sheet 1 is a photograph of the new and distinct variety showing the dwarf globose habit, with densely arranged branches, persistently leafy to the lower branches.

Sheet 2 is a photograph of the *Leucophyllum frutescens* "Compacta" and new and distinct variety "Bertstar Dwarf" showing the greater number of lateral buds and elongation of the stems from those lateral buds, thus the dense habit of the new variety.

Figure 1:
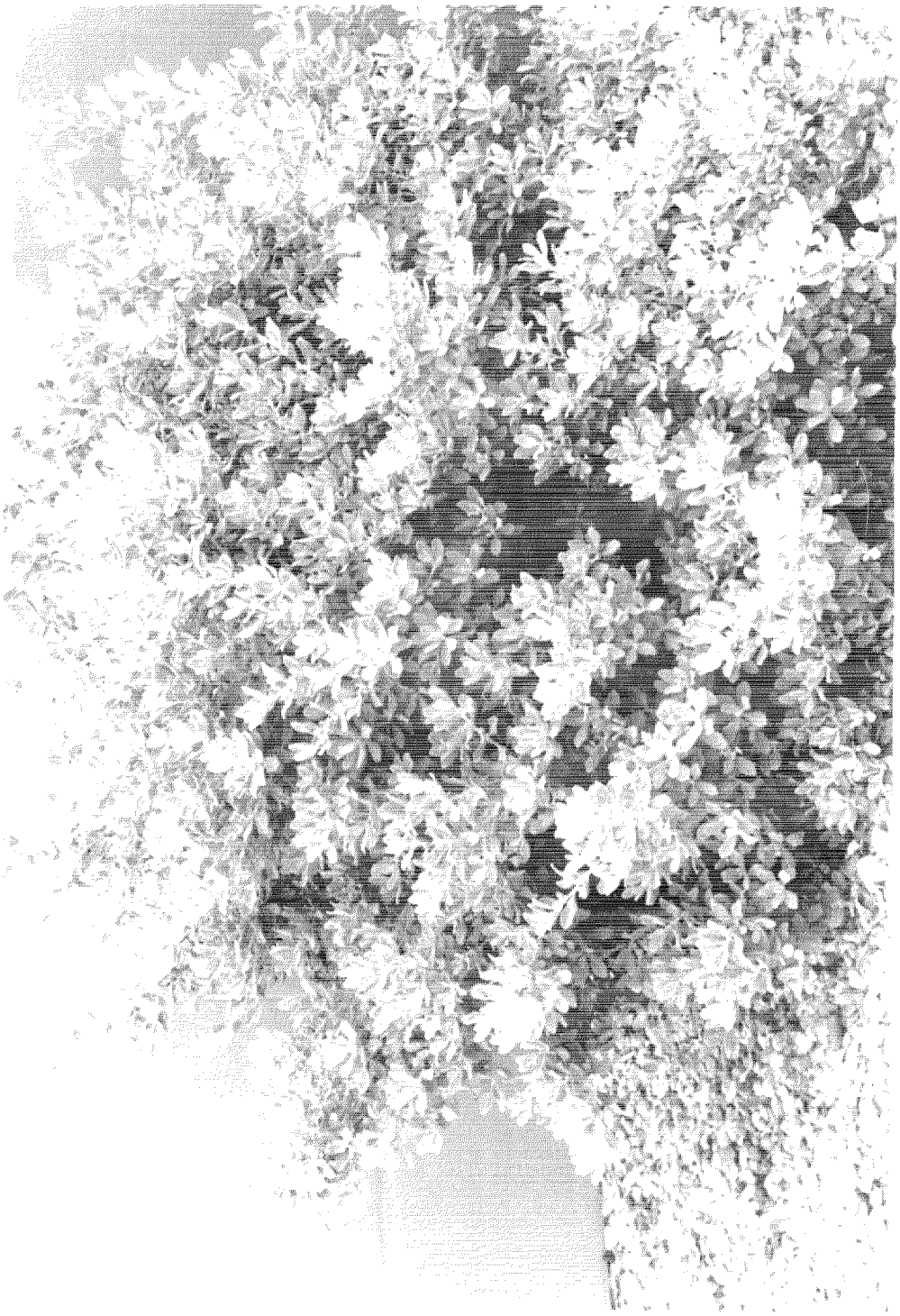
Figure 2:
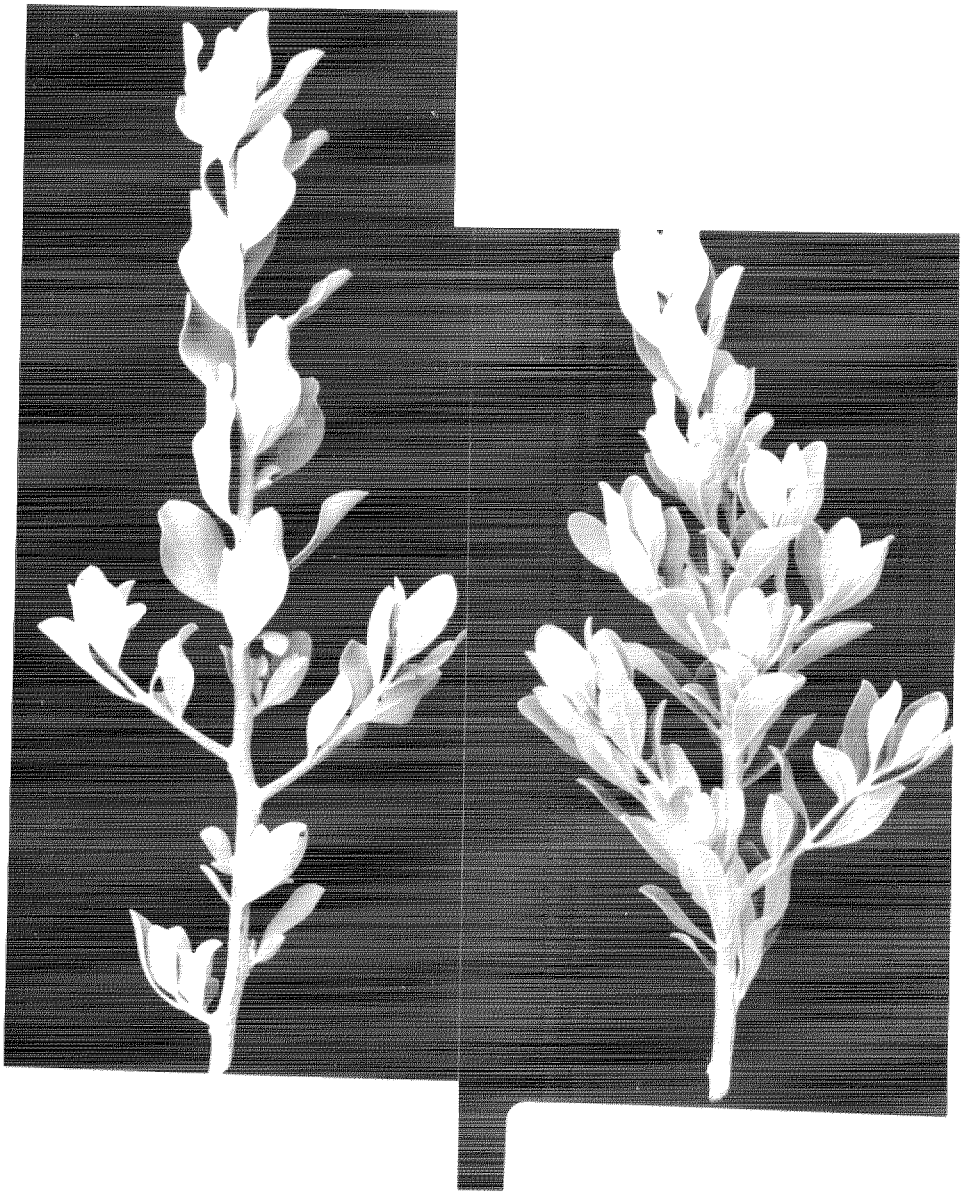
Figure 3:
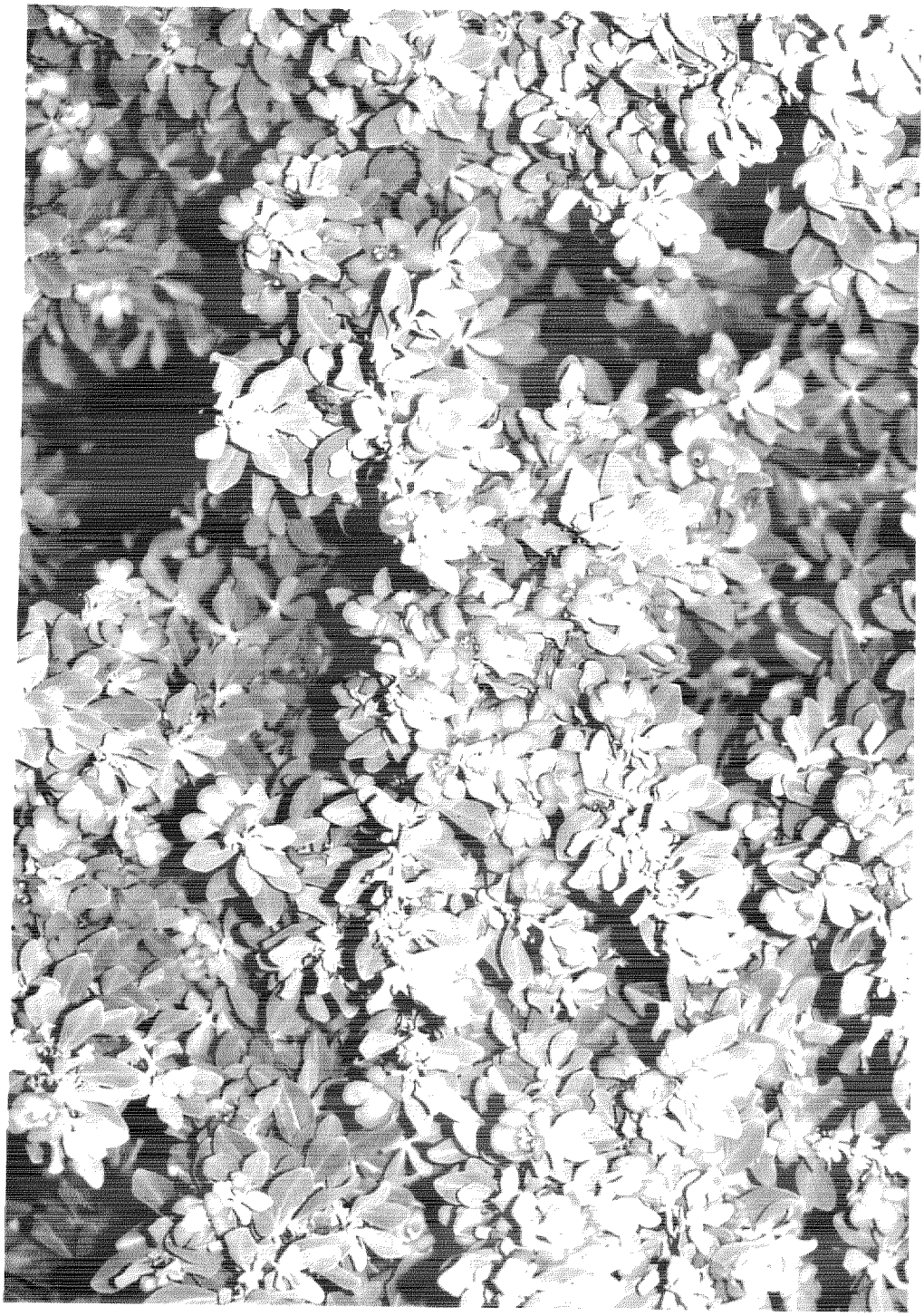
Figure 4:
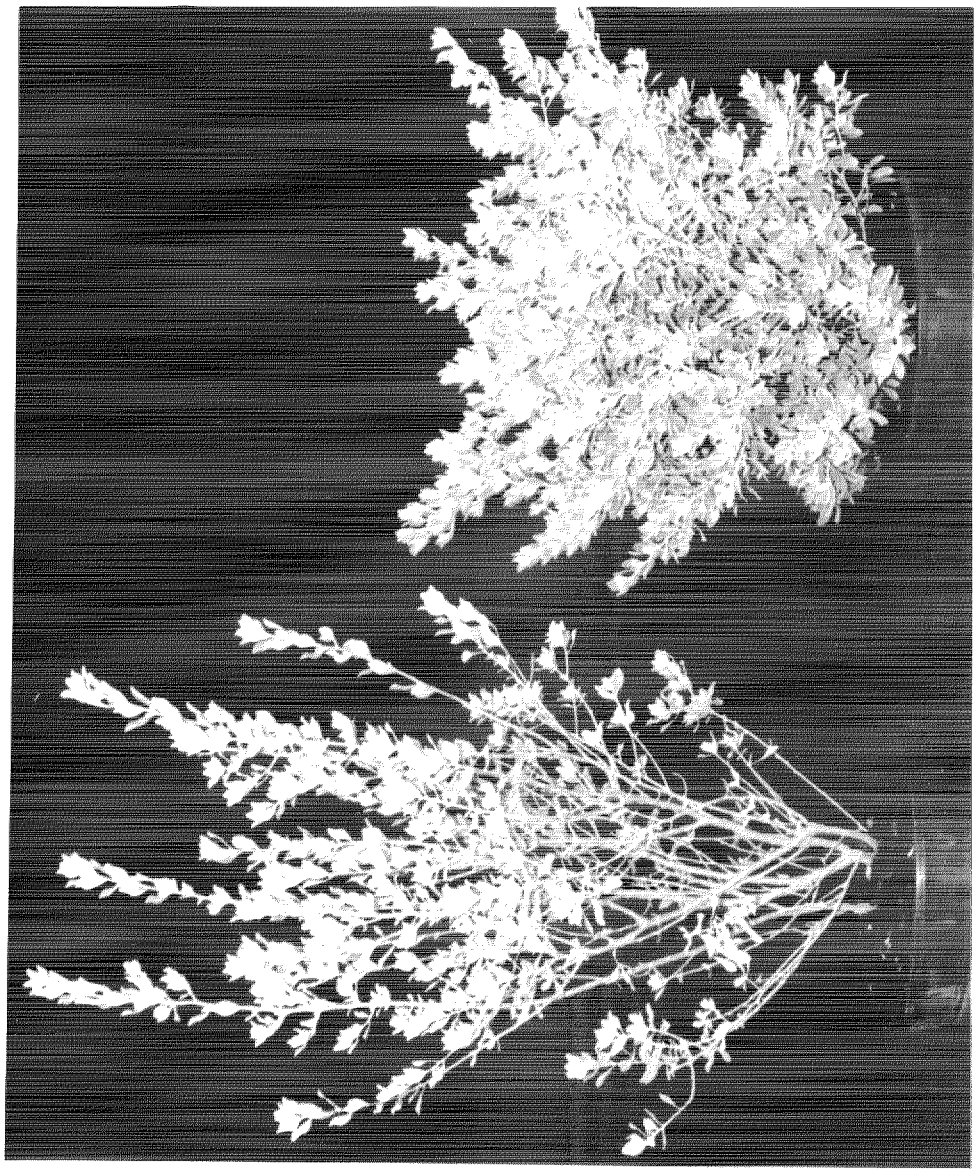

Sheet 3 is a photograph of the new and distinct variety showing the profuse blooming characteristics and dense branching arrangement.

Sheet 4 is a photograph of the overall form of the *Leucophyllum frutescens* "Compacta" and the new variety "Bertstar Dwarf" with persistence of the leaves in the winter. The photograph of sheet 4 was taken in January 1997.

BOTANICAL DESCRIPTION OF THE PLANT

Compactly globose, alternately branched, densely leafy, evergreen shrubs 4 feet tall and wide at maturity (measured at 6 years). Leaves and young twigs silver-grey tomentose with dendritic trichomes; bark of older stems grayish to black and roughened. Leaves alternate to subopposite, obovate to oblong, cuneate-based, apically rounded, 10–25 mm long, 5–15 mm wide, silver-gray tomentose on both surfaces but usually greener on the upper surface, petiole 1–2 mm long, margins entire. Flowers solitary or (less commonly) paired in leaf axils, calyx divided to near base into 5 lightly tomentose, lanceolate lobes 6–7 cm long and 5–6 mm side; corollas funnel form-ampliate with a broad tube 22–25 mm long and 13–15 mm wide at the throat, with 5 abruptly flaring lobes 10–11 mm long and 8–10 mm wide, rose-lavender to reddish-pink, glabrous on outer surfaces but spreading-hairy within, the tube floor with a white patch marked with rows of gold-brown dots; stamens 4, didynamous, included filaments adnate to the corolla tube base for ¼–⅓ their length; anthers yellowish to white, glabrous; styles terminal, cylindrical, straight, 9–14 mm long. Fruit a 2-locular, glabrous, apiculate capsule dehiscing first septicidally to near the base, then loculicidally halfway to the base; seeds 15–25 per locule, small, irregularly ovoid, yellowish brown, minutely reticulate, smooth to somewhat angled.

Measurements (metric) have been taken from the original selection grown in full sun with supplemental irrigation when necessary. Fruit and seed morphology is essentially identical among all forms of the species. Terminology is in accordance with standard botanical usage.

The plant is sharply distinguishable from other forms of *Leucophyllum frutescens* in its shape and leafiness but not in other features of pubescence, leaf morphology, flowers, fruits, or seeds. The new variety is slightly differentiated but overlapping in two floral and foliage features: (a) flowers average slightly larger and wider at the throat than in typical *Leucophyllum frutescens*; and (b) the foliage color is nearly intermediate between the green of the "Green Cloud" cultivar and the more silvery color of both the upper and lower leaf surfaces of the "Compacta" cultivar.

Vigor And Growth Of The Plant

Cold hardiness: Having been transplanted into the landscape in Austin, Tex., and then moved to San Antonio, this new variety has been evaluated through 5 winters with no adverse affects. These areas fall into USDA zone 8.

Conditions for best growth: Cenizo require well drained soils. They are no pH sensitive and are very drought tolerant. They do best in full sun and medium to low humidity.

Flowering period: The new variety, as with the native species, cycle blooming with periods of high heat and increases in humidity thus often called the Barometer plant. They bloom profusely during those periods.

Use of the new variety: Cenizo's are typically used for specimens and in mass such as hedges. This new variety offers a superior form and habit with its dwarf nature and dense habit making it more versatile for low foundational plantings and formal landscapes. Less maintenance will also be needed as this new variety will need no shearing to keep it manageable unlike other cultivars or the native species.

The persistence foliage to the lower portions of the plant through the winter adds to its appeal in the landscape. This new variety is a vigorous grower and does not exhibit the extreme sensitivity to high humidity or over watering that other *Leucophyllum frutescens* cultivars do.

We claim:

1. A new and distinct variety of Cenizo shrub, herein shown and described, characterized by its small, globose habit with densely arranged branches, persistently leafy to the lower and proximal protions of the branches.

* * * * *